United States Patent
Oishi et al.

(10) Patent No.: US 7,104,110 B2
(45) Date of Patent: Sep. 12, 2006

(54) CONTROL DEVICE USED FOR A GAS SENSOR

(75) Inventors: Hidetoshi Oishi, Wako (JP); Hirotoshi Inoue, Wako (JP); Takashi Saito, Wako (JP); Takashi Sasaki, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 151 days.

(21) Appl. No.: 10/938,295

(22) Filed: Sep. 10, 2004

(65) Prior Publication Data
US 2005/0061055 A1     Mar. 24, 2005

(30) Foreign Application Priority Data
Sep. 19, 2003   (JP)   ............................. 2003-328927

(51) Int. Cl.
*G01N 21/00*   (2006.01)
(52) U.S. Cl. ...................................... 73/1.06
(58) Field of Classification Search .................. 73/1.06
See application file for complete search history.

(56) References Cited

FOREIGN PATENT DOCUMENTS

JP       A-6-223850       8/1994

*Primary Examiner*—Robert Raevis
(74) *Attorney, Agent, or Firm*—Hamre, Schumann, Mueller & Larson, P.C.

(57) ABSTRACT

A control device determines whether or not the detected value of a unit conducting current output from a current sensor at least plural times is equal to or greater than a predetermined upper limit current at time of the start of the actuation of a gas sensor, and furthermore, determines that each of the units of the gas sensor is set in an abnormal state if a duration for a state in which it is determined that the detected value of the unit conducting current is equal to or greater than the predetermined upper limit current is equal to or longer than a predetermined upper limit time. On the other hand, if the duration for the state in which it is determined that the detected value of the unit conducting current is equal to or greater than the predetermined upper limit current is shorter than the predetermined upper limit time, it is determined that the detected value of the unit conducting current temporarily becomes equal to or greater than the predetermined upper limit current and each of the units is set in a normal state.

4 Claims, 4 Drawing Sheets

FIG. 6
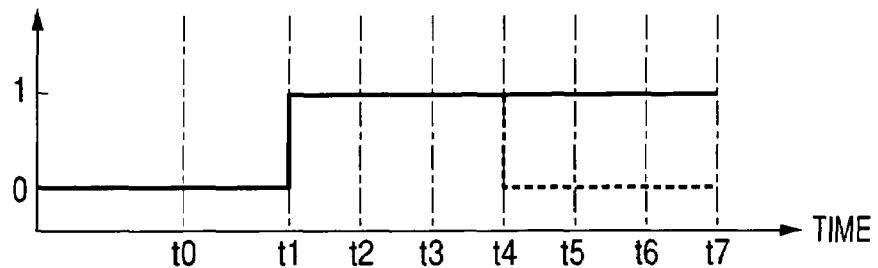
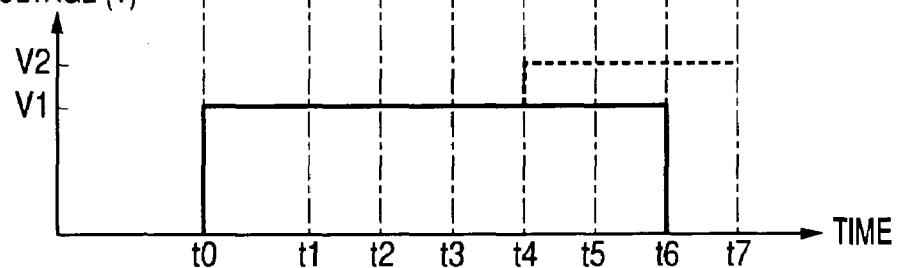
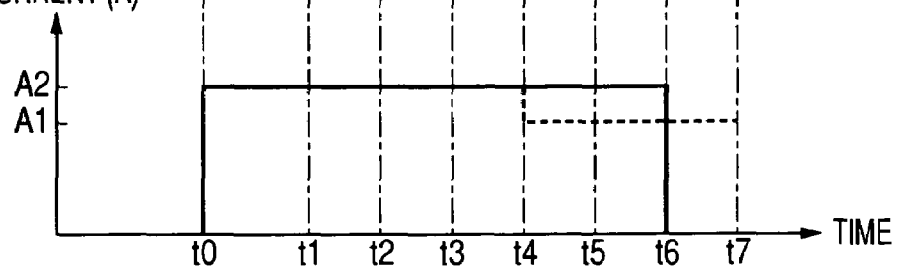
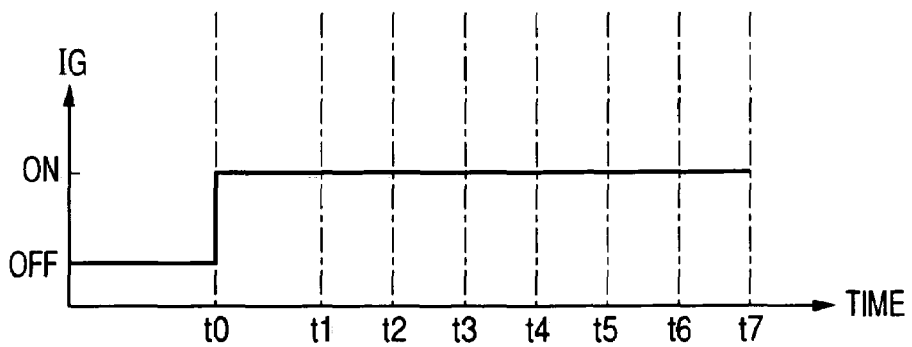

CONTROL DEVICE USED FOR A GAS SENSOR

This application claims foreign priority based on Japanese Patent application No. 2003-328927, filed Sep. 19, 2003, the contents of which is incorporated herein by reference in its entirety.

BACKGROUND OF THE INVENTION

1. Field of the Invention

The present invention relates to a control device of a gas sensor such as a contact combustion type hydrogen sensor to be mounted on a fuel cell vehicle.

2. Description of the Related Art

For example, conventionally, a solid polymer electrolyte fuel cell comprises a stack (hereinafter referred to as a fuel cell), which is constituted by stacking a plurality of cells on a cell formed by interposing a solid polymer electrolyte membrane between a fuel electrode and an oxygen electrode from both sides. Hydrogen is supplied as a fuel to the fuel electrode and air is supplied as an oxidizing agent to the oxygen electrode, and a hydrogen ion generated by a catalytic reaction at the fuel electrode passes through the solid polymer electrolyte membrane and moves to the oxygen electrode, and causes an electrochemical reaction to oxygen at the oxygen electrode, thereby generating a power.

Referring to a fuel cell such as the solid polymer electrolyte fuel cell, there has conventionally been known a protecting device comprising a hydrogen detector (a gas sensor) in a discharge system on an oxygen side of the fuel cell and serving to block the supply of a fuel when detecting that hydrogen on a fuel electrode side leaks toward the oxygen electrode side through a solid polymer electrolyte membrane by means of the hydrogen detector such as disclosed in JP-A-6-223850.

As for the hydrogen detector, moreover, there has been known a hydrogen detector of a gas contact combustion type which comprises a pair of a gas detecting unit formed of a catalyst such as platinum and a temperature compensating unit and serves to detect the concentration of a hydrogen gas depending on a difference in an electrical resistance generated together with the temperature compensating unit set in a relatively low temperature state such as an atmospheric temperature when the gas detecting unit is brought into a relatively high temperature state by heat generated through a combustion in the contact of hydrogen with the catalyst such as platinum.

In the gas sensor described above, the abnormal state of the gas sensor, for example, the presence of a short circuit is detected based on the detected value of the conducting current of each unit. For example, in the case in which the detected value of the conducting current is increased to exceed a predetermined decision threshold, it is determined that the short circuit is caused by an unrecoverable breakage generated on each unit or an abnormality generated on a circuit system, and the operation of the gas sensor is thus stopped.

In the fuel cell such as the solid polymer electrolyte fuel cell described above, however, water (humidifying water) is mixed with a reaction gas supplied to the fuel cell (for example, hydrogen or air) by means of a humidifier in order to maintain the ion conductivity of the solid polymer electrolyte membrane, and furthermore, reaction product water is generated by an electrochemical reaction during the operation of the fuel cell. For this reason, an exhaust gas of the fuel cell, particularly, an exhaust gas on an oxygen electrode side has a high wettability.

In the protecting device of the fuel cell according to an example of the conventional art, therefore, a dew condensation is generated on a hydrogen detector provided in the passage for an off-gas having a high wettability which is discharged from the fuel cell due to the off-gas in some cases. In some cases in which the hydrogen detector of a gas contact combustion type is particularly provided in a discharge system on the oxygen electrode side of the fuel cell, the detected value of an conducting current is increased to exceed a predetermined decision threshold due to a short circuit caused by the condensed water when the current conductance is carried out in a state in which the humidifying water or the reaction product water is stuck onto a gas detecting unit, and it is determined that an unrecoverable abnormality is generated on the gas sensor and the operation of the gas sensor is thus stopped even if the dew condensation is temporarily generated.

SUMMARY OF THE INVENTION

The invention has been made in consideration of the circumstances and has an object to provide a control device of a gas sensor which can properly detect the presence of the abnormality of the gas sensor.

In order to solve the problems and to attain the object, a first aspect of the invention is directed to a control device of a gas sensor for detecting a concentration of a detected gas contained in a gas to be inspected based on a difference in an electrical resistance value between a detecting unit (for example, a detecting unit 31 according to an embodiment which will be described below) and a compensating unit (for example, a temperature compensating unit 32 according to the embodiment which will be described below), comprising a current detector (for example, a current sensor according to the embodiment which will be described below) for detecting a current conducted to the detecting unit and the compensating unit, short-circuit determination means (for example, a step S13 according to the embodiment which will be described below) for determining, at plural times, whether or not a detected value of the conducting current which is detected by the current detector is equal to or greater than a predetermined threshold, and abnormality determination means (for example, a step S15 according to the embodiment which will be described below) for determining an abnormal state of the detecting unit and the compensating unit, wherein said abnormal state is determined under such a condition that a duration time of a determination state of the detected value of the conducting current being equal to or greater than the predetermined threshold by the short-circuit detecting means is equal to or longer than a predetermined time (for example, a predetermined upper limit time according to the embodiment which will be described below).

According to the control device of a gas sensor having the structure described above, it is determined, at plural times, whether or not the short-circuit state in which the detected value of the conducting current is equal to or greater than the predetermined threshold is set by the short-circuit determination means. Consequently, it is possible to determine whether or not the detected short-circuit state can be eliminated in a shorter time than the predetermined time as in a state in which a dew condensation is temporarily generated on the surfaces of the detecting unit and the compensating unit, for example. It is possible to operate the gas sensor more properly as compared with the case in which the detecting operation of the gas sensor is stopped when the short-circuit state is detected, for example.

Furthermore, a second aspect of the invention is directed to the control device of a gas sensor, further comprising current conductance control means (for example, a control device 2 according to the embodiment which will be described below) for continuously conducting the detecting unit and the compensating unit when determining that the detected value of the conducting current is equal to or greater than the predetermined threshold by the short-circuit determination means.

According to the control device of a gas sensor having the structure described above, also in the case in which the dew condensation is temporarily generated on the surfaces of the detecting unit and the compensating unit so that the detected value of the conducting current is equal to or greater than the predetermined threshold, for example, it is possible to rapidly evaporate condensed water which is generated because of a rise in a temperature with continuous current conductance to the detecting unit and the compensating unit by the same current conductance.

Moreover, a third aspect of the invention is directed to the control device of a gas sensor, wherein the detecting unit and the compensating unit are provided in a gas detecting chamber for introducing the gas to be inspected, the control device further comprising a heater provided in the gas detecting chamber, and heater current conductance control means (serving as the control device 2 according to the embodiment which will be described below, for example) for continuing or starting to conduct the heater when it is determined that the detected value of the conducting current is equal to or greater than the predetermined threshold by the short-circuit determination means.

According to the control device of a gas sensor having the structure described above, also in the case in which the dew condensation is temporarily generated on the surfaces of the detecting unit and the compensating unit so that the detected value of the conducting current is equal to or greater than the predetermined threshold, for example, it is possible to rapidly evaporate condensed water which is generated on the surfaces of the detecting unit and the compensating unit by continuing or starting to conduct the heater.

Furthermore, a fourth aspect of the invention is directed to the control device of a gas sensor, wherein the predetermined time is equal to or longer than an upper limit time required for evaporating water present on surfaces of at least the detecting unit and the compensating unit.

According to the control device of a gas sensor having the structure described above, it is possible to properly determine whether or not the short-circuit state in which the detected value of the conducting current is equal to or greater than the predetermined threshold is caused by an abnormal state which cannot be recovered in the shorter time than the predetermined upper limit time, that is, the state in which the condensed water is temporarily generated on the surfaces of the detecting unit and the compensating unit when detecting the same short-circuit state.

According to the control device of a gas sensor in accordance with the first aspect of the invention, it is possible to determine whether or not the short-circuit state in which the detected value of the conducting current is equal to or greater than the predetermined threshold can be eliminated in the shorter time than the predetermined time. It is possible to operate the gas sensor more properly as compared with the case in which the detecting operation of the gas sensor is stopped when the short-circuit state is detected, for example.

According to the control device of a gas sensor in accordance with the second aspect of the invention, furthermore, also in the case in which the dew condensation is temporarily generated on the surfaces of the detecting unit and the compensating unit so that the detected value of the conducting current is equal to or greater than the predetermined threshold, for example, it is possible to rapidly evaporate condensed water which is generated because of a rise in a temperature with continuous current conductance to the detecting unit and the compensating unit by the same current conductance.

According to the control device of a gas sensor in accordance with the third aspect of the invention, moreover, also in the case in which the dew condensation is temporarily generated on the surfaces of the detecting unit and the compensating unit so that the detected value of the conducting current is equal to or greater than the predetermined threshold, for example, it is possible to rapidly evaporate the condensed water which is generated on the surfaces of the detecting unit and the compensating unit by continuing or starting to conduct the heater.

According to the control device of a gas sensor in accordance with the fourth aspect of the invention, furthermore, it is possible to properly determine whether or not the short-circuit state in which the detected value of the conducting current is equal to or greater than the predetermined threshold is caused by an abnormal state which cannot be recovered in the shorter time than the predetermined upper limit time, that is, the state in which the condensed water is temporarily generated on the surfaces of the detecting unit and the compensating unit when detecting the same short-circuit state.

BRIEF DESCRIPTION OF THE DRAWINGS

FIG. 6 is a graph showing an example of a temporal change in the amounts of current conductance to each of units and a heater in the gas sensor according to the embodiment illustrated in FIG. 1 and a temporal change in the flag value of a short-circuit determining flag.

DESCRIPTION OF THE PREFERRED EMBODIMENTS

A gas sensor according to an embodiment of the invention will be described below with reference to the accompanying drawings.

Figure 1:
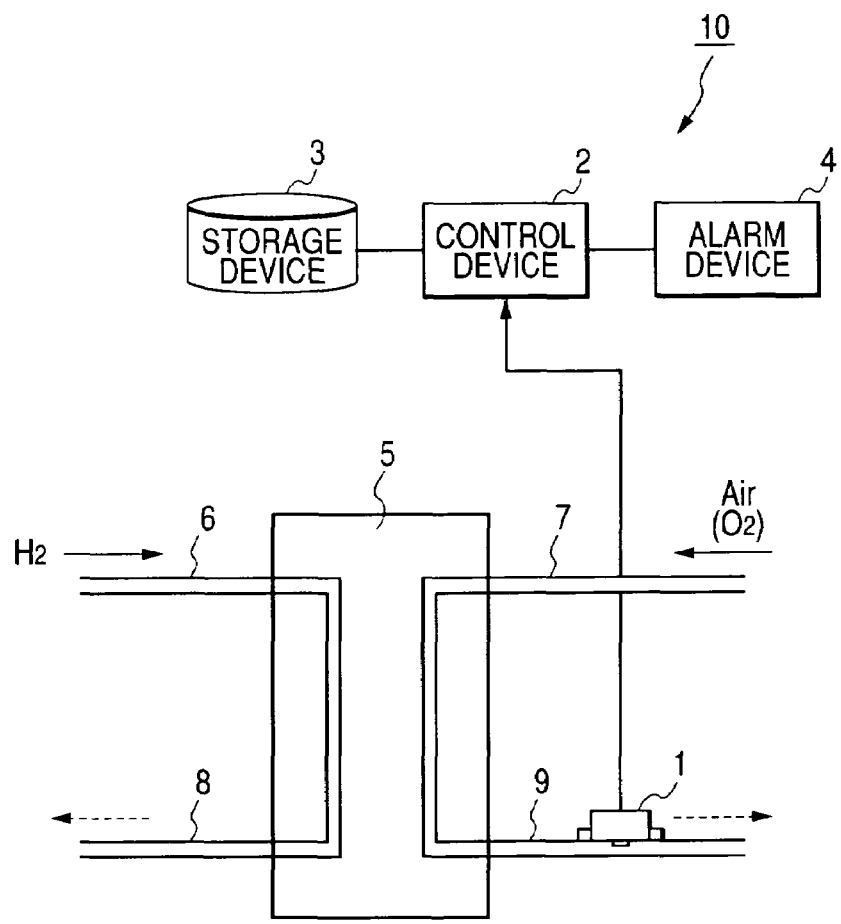
FIG. 1 is a diagram showing the structure of the main part of a fuel cell system comprising a gas sensor according to an embodiment of the invention.

A gas sensor 1 according to the embodiment constitutes a hydrogen sensor for detecting hydrogen, for example, and is provided on an outlet side piping 9 at an oxygen electrode side and serves to confirm that the hydrogen is not discharged from the outlet side piping 9 in a fuel cell system 10 comprising a control device 2, a storage device 3, an alarm device 4, a fuel cell 5 to be the power source of a vehicle, and pipings 6, 7, 8 and 9 connected to the fuel cell 5 and serving to supply a reaction gas as shown in FIG. 1, for example.

The control device 2 is connected to the gas sensor 1 attached to the outlet side piping 9 on the oxygen electrode side and determines whether or not the abnormal state of the fuel cell 5 is generated according to the result of a comparison between a detection signal output from the gas sensor 1 and a predetermined decision threshold stored in the storage device 3, and outputs an alarm through the alarm device 4 when determining that the abnormal state is set, for example. The storage device 3 stores the map of a predetermined decision threshold for the detected value of the gas sensor 1 corresponding to the operation state of the fuel cell 5, for example, a differential pressure between electrodes or an operating pressure.

The fuel cell 5 is mounted on a vehicle as the power source of an electric vehicle, for example, and a membrane electrode assembly interposing a solid polymer electrolyte membrane formed by a cation exchange membrane between a fuel electrode and an oxygen electrode is further constituted by stacking a large number of sets of fuel cells (not shown) interposed between pairs of separators, for example.

The hydrogen is ionized over the catalytic electrode of the fuel electrode by the fuel gas such as the hydrogen supplied from the inlet side piping 6 to the fuel electrode and is moved to the oxygen electrode through the solid polymer electrolyte membrane which is properly humidified. An electron generated at that time is taken out into an external circuit and is utilized as a DC electrical energy. An oxidizing agent gas such as oxygen or air is supplied to the oxygen electrode through the inlet side piping 7. For this reason, a hydrogen ion, an electron and oxygen react so that water is produced at the oxygen electrode.

Then, a so-called off-gas which has already been subjected to the reaction is discharged from the outlet side pipings 8 and 9 to the outside of a system at both the fuel electrode side and the oxygen electrode side.

Figure 2:
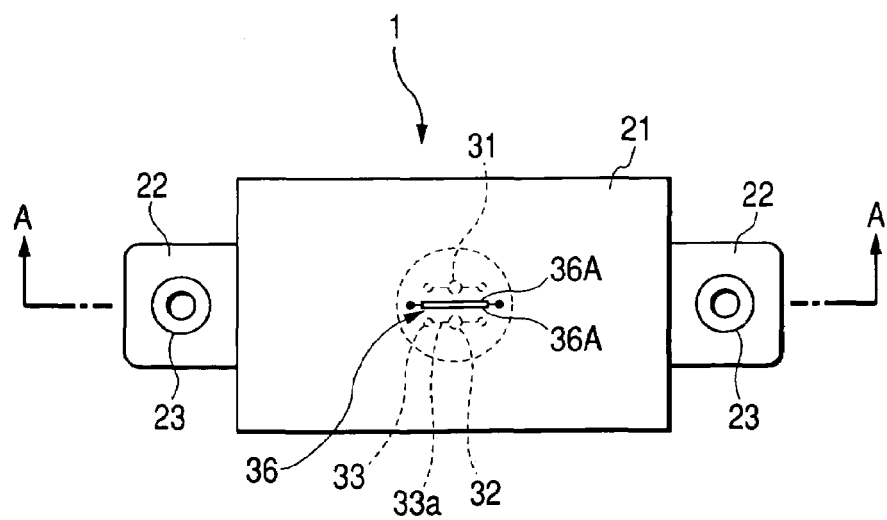
FIG. 2 is a sectional view showing the gas sensor illustrated in FIG. 1.
Figure 3:
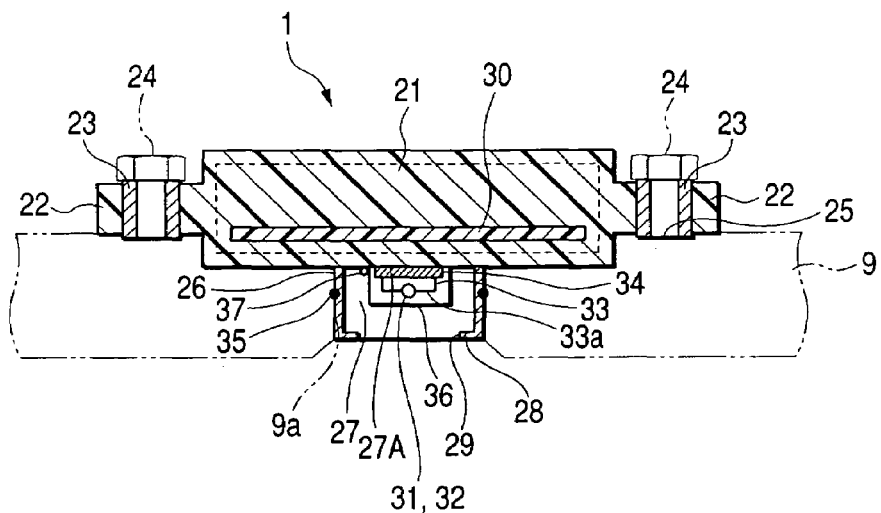
FIG. 3 is a schematic sectional view taken along an A—A line in FIG. 2.

For example, as shown in FIGS. 2 and 3, the gas sensor 1 comprises a case 21 taking the shape of a rectangular parallelepiped which is long in the longitudinal direction of the outlet side piping 9 extended in a horizontal direction, that is, the horizontal direction. The case 21 is formed of polyphenylene sulfide and includes a flange portion 22 on both ends in a longitudinal direction.

A collar 23 is attached to the flange portion 22 and a bolt 24 is inserted into the collar 23 so that the flange portion 22 is fastened and fixed to a mounting seat 25 provided on the outlet side piping 9 at the oxygen electrode side as shown in FIG. 3, for example.

As shown in FIG. 3, for example, a cylindrical portion 26 is formed on the end face of the case 21 in the direction of a thickness, the inner part of the cylindrical portion 26 is formed as a gas detecting chamber 27, a flange portion 28 is inward formed on the inner side surface of the gas detecting chamber 27, and the inner peripheral portion of the flange portion 28 is opened as a gas introducing portion 29.

A circuit board 30 sealed with a resin is provided in the case 21 and a detecting unit 31 and a temperature compensating unit 32 which are provided in the cylindrical portion 26 are connected to the circuit board 30. The units 31 and 32 are provided to make a pair at a predetermined interval in a position placed apart by a predetermined distance in the direction of the thickness of the gas sensor 1 from a base 34 disposed on a bottom surface 27A of the gas detecting chamber 27 through a plurality of, for example, four stays 33 for current conductance and a lead wire 33a which are connected to the circuit board 30. Moreover, a seal member 35 is attached to the outer peripheral surface of the cylindrical portion 26 and is provided in close contact with the inner peripheral wall of a through hole 9a of the outlet side piping 9, thereby maintaining an airtightness.

Figure 4:
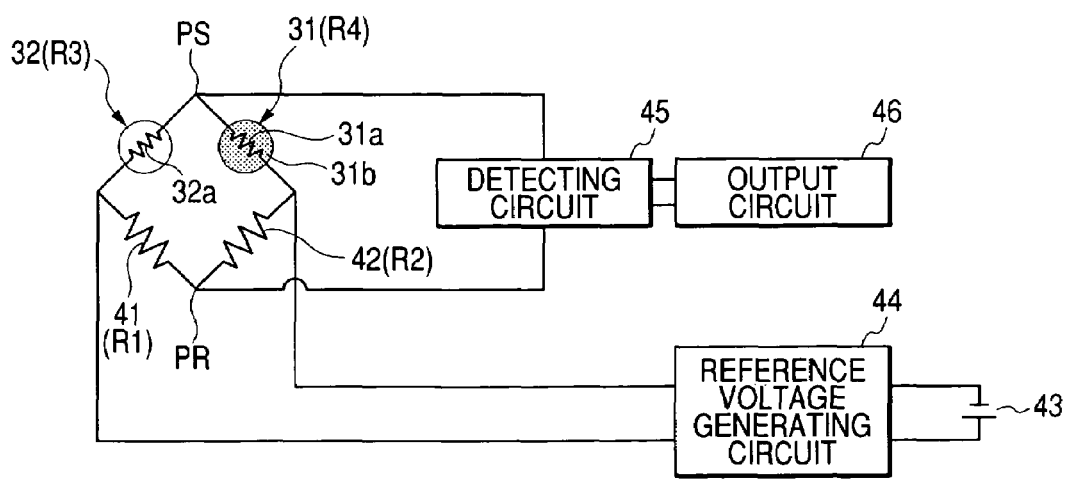
FIG. 4 is a circuit diagram showing the gas sensor illustrated in FIG. 1.

The detecting unit 31 is well known and the surface of a coil 31a of a metal wire including platinum having a high temperature coefficient to an electrical resistance is covered with a carrier such as alumina carrying a catalyst 31b formed of an active noble metal to hydrogen to be a detected gas as shown in FIG. 4, for example.

The temperature compensating unit 32 is inactive to the detected gas and the surface of a coil 32a which is equivalent to that of the detecting unit 31 is covered with a carrier such as alumina, for example.

By utilizing the fact that a difference in an electrical resistance value is made between the detecting unit 31 having a temperature raised by the heat of a combusting reaction which is generated when the hydrogen to be the detected gas comes in contact with the catalyst 31b of the detecting unit 31 and the temperature compensating unit 32 having a lower temperature than the detecting unit 31 because of no generation of the combusting reaction by the detected gas, it is possible to offset a change in the electrical resistance value based on an atmospheric temperature, thereby detecting the concentration of the hydrogen.

For example, as shown in FIG. 2, a heater 36 taking the shape of an almost rectangular plate is provided in an erecting state in the direction of the flow of the detected gas in order to block both the detecting unit 31 and the temperature compensating unit 32 therebetween in the gas detecting chamber 27. The heater 36 is constituted by a resistor member and is conducted by the circuit board 30, thereby heating the inner part of the gas detecting chamber 27 and the units 31 and 32, and is provided with a radiating surface 36A directed toward the detecting unit 31 and the temperature compensating unit 32. In other words, each surface of the heater 36 is constituted as the radiating surface 36A. The detected gas flowing through the heater 36 is distributed evenly into the detecting unit 31 and the temperature compensating unit 32.

Moreover, a sensor 37 for detecting a temperature and a humidity in the gas detecting chamber 27 is attached to the gas detecting chamber 27.

For example, as shown in FIG. 4, in a bridge circuit in which a branch side having the detecting unit 31 (a resistance value R4) and the temperature compensating unit 32 (a resistance value R3) connected in series and a branch side having a fixed resistor 41 (a resistance value R1) and a fixed resistor 42 (a resistance value R2) connected in series are connected in parallel with a reference voltage generating circuit 44 for applying a predetermined reference voltage based on a voltage supplied from an external power supply 43, a detecting circuit 45 for detecting a voltage between a node PS of the detecting unit 31 and the temperature compensating unit 32 and a node PR of the fixed resistors 41 and 42 is connected between the nodes PS and PR, and furthermore, an output circuit 46 is connected to the detecting circuit 45.

When the hydrogen to be the detected gas is not present in a gas to be inspected which is introduced into the gas detecting chamber 27, the bridge circuit is balanced in a state of R1×R4=R2×R3 and the output of the detecting circuit 45 becomes zero. On the other hand, when the hydrogen is present, it is combusted in the catalyst 31b of the detecting unit 31 and the temperature of the coil 31a is raised so that the resistance value R4 is increased. On the other hand, the hydrogen is not combusted in the temperature compensating unit 32 so that the resistance value R3 is not changed. Consequently, the balance of the bridge circuit is broken so that a proper voltage to be changed in a tendency of an increase corresponding to a change in the increase of the concentration of the hydrogen is applied to the detecting circuit 45. The detected value of the voltage output from the detecting circuit 45 is output to the output circuit 46, and the output circuit 46 outputs the input detected value to the control device 2. In the control device 2, the concentration of the hydrogen is calculated based on the map of the concentration of the hydrogen which is preset corresponding to a change in the detected value of the voltage.

The control device 2 is connected to the sensor 37 and the heater 36 in the gas detecting chamber 27, and controls the actuation states of the units 31 and 32 and the heater 36, for example, each of timings for starting and stopping current conductance and the amount of the current conductance depending on the state of a temperature or a humidity in the atmosphere in the gas detecting chamber 27 which is output from the sensor 37, and the load state and operation state of the fuel cell 5, for example. At this time, the control device 2 controls the amount of the current conductance to the heater 36 through a feedback control for the value of a current to be conducted to the heater 36 or a chopper control based on the ON/OFF operation of a switching unit (that is, the ON/OFF switching control of the current conductance), for example.

For example, the control device 2 controls the current conductance to the heater 36 based on a temperature detected by the sensor 37, and controls the timings for starting and stopping the current conductance to the heater 36 and the amount of the current conductance in such a manner that a temperature in the gas detecting chamber 27 which is detected from the sensor 37 is set within a predetermined temperature range which is higher than at least a dew-point temperature and a relative humidity in the gas detecting chamber 27 which is detected from the sensor 37 has the retrieved value of a relative humidity within a predetermined humidity range or a relative humidity obtained from the map of a relative humidity corresponding to a temperature condition in the gas detecting chamber 27 which is previously created, for example.

Furthermore, the control device 2 controls the amount of the current conductance to the heater 36 corresponding to the operation state of the fuel cell 5 (that is, an actuation state including the start and stop of the actuation of the fuel cell 5), a load state in the operation of the fuel cell 5, and the power generating state of the fuel cell 5 which is calculated based on a power generating command to be given to the fuel cell 5 (an FC output command value), the current value of the output current of the fuel cell 5 which is detected by an output current sensor (not shown), and the detected value of the flow of air supplied from an air compressor (not shown) to the fuel cell 5 which is detected by a flow sensor (not shown) in addition to the temperature state in the gas detecting chamber 27 which is detected by the sensor 37, for example.

For example, in the case in which the load state of the fuel cell 5 is changed into a high load state and there is a possibility that the flow of an off-gas flowing in the outlet side piping 9 on the oxygen electrode side might be increased to drop the temperature in the gas detecting chamber 27 of the gas sensor 1 exposed to the off-gas, and the amount of water produced in the fuel cell 5 and contained in the off-gas might be increased to increase the relative humidity in the gas detecting chamber 27, the control device 2 increases the amount of the current conductance to the heater 36 to raise the temperature in the gas detecting chamber 27, thereby preventing the generation of a dew condensation in the gas detecting chamber 27. On the other hand, in the case in which the load state of the fuel cell 5 is changed into a low load state, the control device 2 decreases the amount of the current conductance to the heater 36, thereby suppressing an excessive energy consumption.

In the case in which the flow of the off-gas fluidizing in each of the outlet side pipings 8 and 9 is increased so that a purging process for discharging water remaining in a fuel cell system to an outside is executed when the actuation of the fuel cell 5 is stopped, for example, the control device 2 increases the amount of the current conductance to the heater 36 to temporarily raise the temperature in the gas detecting chamber 27, thereby increasing the amount of saturated vapor of an atmospheric gas in the gas detecting chamber 27 to prevent the generation of the dew condensation in the gas detecting chamber 27.

Moreover, the control device 2 starts to conduct the units 31 and 32 and the heater 36 in the gas sensor 1 prior to the start of the fluidization of the off-gas in the outlet side piping 9 on the oxygen electrode side when the actuation of the fuel cell 5 is started, and stops the fluidization of the off-gas in the outlet side piping 9 on the oxygen electrode side and then stops the current conductance to the units 31 and 32 and the heater 36 in the gas sensor 1 when the actuation of the fuel cell 5 is stopped.

The detecting system of the gas sensor 1 is provided with a current sensor (not shown) for detecting the current value of a unit conducting current to be supplied to each of the units 31 and 32, and the control device 2 determines whether or not the detected value of the unit conducting current output from the current sensor is equal to or greater than a predetermined threshold, thereby detecting that a short circuit is generated on the detecting system of the gas sensor 1 or not as will be described below.

For example, the control device 2 determines whether or not the detected value of the unit conducting current output from the current sensor at least plural times is equal to or greater than a predetermined upper limit current as will be described below when the actuation of the gas sensor 1 is started, and determines that each of the units 31 and 32 is set in an abnormal state if a duration for which it is determined that the detected value of the unit conducting current is equal to or greater than the predetermined upper limit current is equal to or longer than a predetermined upper limit time. On the other hand, if the duration for the decision state is shorter than the predetermined upper limit time, it is determined that the detected value of the unit conducting current temporarily becomes equal to or greater than the predetermined upper limit current and each of the units 31 and 32 is set in a normal state.

More specifically, also when detecting the generation of the short circuit in which the detected value of the unit conducting current output from the current sensor is equal to or greater than a predetermined threshold, the control device 2 can determine that each of the units 31 and 32 is set in the normal state, thereby continuing the detecting operation of the gas sensor 1 when the short circuit is eliminated if the short-circuit state is caused by an abnormal state which cannot be recovered in a shorter time than the predetermined upper limit time. The abnormal state which cannot be recovered in the shorter time than the predetermined upper limit time implies a state in which condensed water is present on the surface of each of the units 31 and 32 when the actuation of the gas sensor 1 is started, for example. In this case, even if the short circuit is temporarily detected with the start of the current conductance to each of the units 31 and 32, it is possible to evaporate the condensed water from the surface of each of the units 31 and 32 to eliminate the short circuit by continuing the current conductance to each of the units 31 and 32, and furthermore, starting the actuation of the heater 36. On the other hand, the abnormal state which cannot be recovered in the shorter time than the predetermined upper limit time implies a state in which each of the units 31 and 32 is broken or deteriorated, for example.

Next, description will be given to the operation of the control device of the gas sensor according to the embodiment, particularly, an abnormal decision processing in the start of the actuation of the gas sensor 1.

Figure 5:
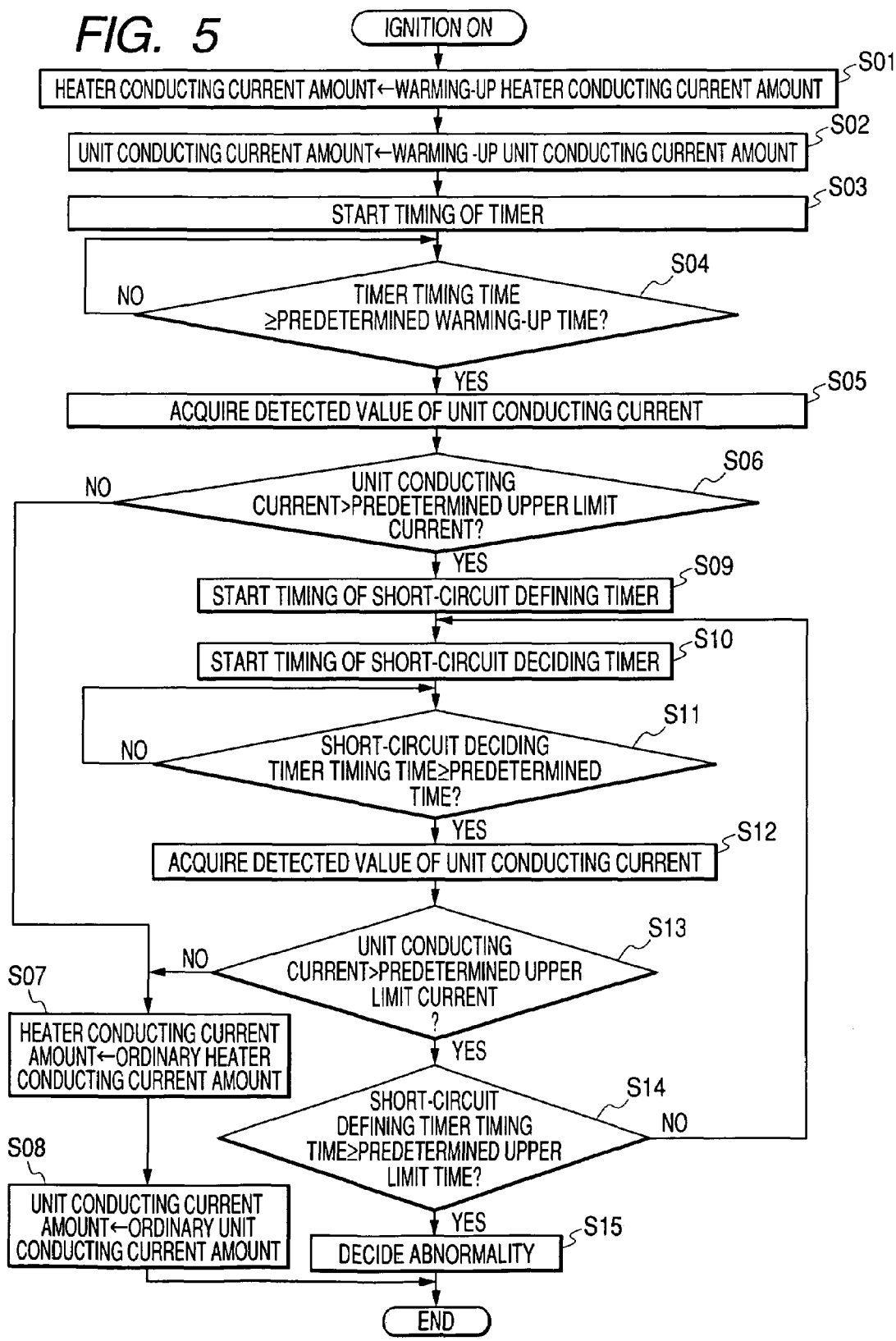
FIG. 5 is a flow chart showing an abnormality decision processing at time of the start of the operation of the control device of the gas sensor illustrated in FIG. 1, particularly, the actuation of the gas sensor.

First of all, for example, when the ignition switch (IG) of a vehicle is turned ON by a driver's operation at a time t0 shown in FIG. 6, processings in and after a step S01 shown in FIG. 5 are executed.

For example, at the step S01 shown in FIG. 5, a predetermined warming-up heater current conductance amount (an conducting current A2 shown in FIG. 6, for example) is set to be a heater current conductance amount to the heater 36 (for example, an conducting current).

At a step S02, then, a predetermined warming-up unit current conductance amount (for example, an conducting voltage V1 shown in FIG. 6) is set to be the amount of current conductance to each of the units 31 and 32 (for example, an conducting voltage). The warming-up unit current conductance amount causes a thermal stress generated in each of the units 31 and 32 to have a predetermined value or less and prevents a breakage or a deterioration from being caused by the thermal stress generated on each of the units 31 and 32 also in the case in which the current conductance is carried out over each of the units 31 and 32 stepwise in a state in which the amount of current conductance to the heater 36 is set to be the predetermined warming-up heater current conductance amount, and the same amount is obtained by a predetermined experiment, for example.

At a step S03, next, the timing of a warming-up continuation timer is started.

At a step S04, subsequently, it is determined whether or not the timer value of the warming-up continuation timer is equal to or greater than a predetermined warming-up time.

If the result of the decision is "NO", the processing of the step S04 is repeated.

On the other hand, if the result of the decision is "YES", the timer value of the warming-up continuation timer is reset and the processing proceeds to a step S05.

At the step S05, then, the detected value of a unit conducting current which is detected by the current sensor is acquired.

At a step S06, thereafter, it is determined whether or not the detected value of the unit conducting current thus acquired is equal to or greater than a predetermined upper limit current.

If the result of the decision is "YES", it is determined that a short circuit is generated in the detecting system of the gas sensor 1 and 1 is set to the flag value of a short-circuit determining flag at a time t1 shown in FIG. 6, for example, and the processing proceeds to a step S09 which will be described below.

On the other hand, if the result of the decision is "NO", it is determined that the short circuit is not generated in the detecting system of the gas sensor 1 and the gas sensor 1 is set in a normal state, and the processing proceeds to a step S07.

At the step S07, then, the heater current conductance amount is reduced from the warming-up heater current conductance amount (for example, the conducting current A2 in FIG. 6) to an ordinary heater current conductance amount (for example, the conducting current A1<A2 shown in FIG. 6).

At a step S08, subsequently, the unit current conductance amount is increased from the warming-up unit current conductance amount (for example, the conducting voltage V1 shown in FIG. 6) to an ordinary unit current conductance amount (for example, the conducting voltage V2>V1 shown in FIG. 6), and a serial processing is thus carried out.

At a step S09, the timing of a short-circuit defining timer is started.

At a step S10, next, the timing of a short-circuit determining timer is started.

At a step S11, subsequently, it is determined whether or not the timer value of the short-circuit determining timer is equal to or greater than a predetermined time.

If the result of the decision is "NO", the processing of the step S11 is repeated.

On the other hand, if the result of the decision is "YES", the timer value of the short-circuit determining timer is reset and the processing proceeds to a step S12.

At the step S12, next, the detected value of the unit conducting current which is detected by the current sensor is acquired.

At a step S13, subsequently, it is determined whether or not the detected value of the unit conducting current which is acquired is equal to or greater than the predetermined upper limit current.

If the result of the decision at the step S13 is "NO", it is determined that the gas sensor 1 is set in the normal state because the generated short circuit is eliminated, and the flag value of the short-circuit determining flag is set to be zero as shown in a dotted line after a time t4 shown in FIG. 6, for example, and the processing proceeds to the step S07.

On the other hand, if the result of the decision at the step S13 is "YES", it is determined that the short-circuit state is continuously maintained and the processing proceeds to a step S14.

At the step S14, then, it is determined whether or not the timer value of the short-circuit defining timer is equal to or greater than a predetermined upper limit time. The predetermined upper limit time is required for evaporating the condensed water produced temporarily on at least the surface of each of the units 31 and 32, and is previously obtained by a predetermined experiment, for example.

If the result of the decision is "NO", the processing returns to the step S10.

On the other hand, if the result of the decision is "YES", the timer value of the short-circuit defining timer is reset and the processing proceeds to a step S15.

At the step S15, it is determined that an abnormal state which cannot be recovered in a shorter time than a predetermined upper limit time is generated, and the current conductance to each of the units 31 and 32 and the heater 36 is stopped, thereby halting the detecting operation of the gas sensor 1 at a time t6 shown in FIG. 6, for example. Thus, the serial processing is ended.

As described above, according to the control device of a gas sensor in accordance with the embodiment, it is determined whether or not the short-circuit state generated in the detecting system of the gas sensor 1 is caused by the abnormal state which cannot be recovered in the shorter time than the predetermined upper limit time, for example, the state in which the condensed water is temporarily generated on the surface of each of the units 31 and 32 when the same short-circuit state is detected. Whether the actuation of the gas sensor 1 is continuously carried out is set depending on the result of the decision. Consequently, it is possible to actuate the gas sensor 1 more properly as compared with the case in which the detecting operation of the gas sensor 1 is stopped when the short-circuit state is detected, for example.

In addition, also in the case in which a duration for a state in which a predetermined warming-up unit current conductance amount is set to be a unit current conductance amount and a larger predetermined warming-up heater current conductance amount than an ordinary heater current conductance amount is set to be a heater current conductance amount is equal to or longer than a predetermined warming-up time when the actuation of the gas sensor 1 is started, for example, the state in which the larger predetermined warming-up heater current conductance amount than the ordinary heater current conductance amount is set to be the heater current conductance amount is continuously maintained when the short-circuit state is detected. Consequently, it is possible to more shorten a time required for evaporating the condensed water produced temporarily on the surface of each of the units 31 and 32, that is, a time required for starting the gas sensor 1 for setting the ordinary heater current conductance amount to be the heater current conductance amount and setting the ordinary unit current conductance amount to be the unit current conductance amount as compared with the case in which the heater current conductance amount is reduced from the warming-up heater current conductance amount to the ordinary heater current conductance amount when the duration is equal to or longer than the predetermined warming-up time, for example.

While the state in which the warming-up heater current conductance amount is set to be the heater current conductance amount is continuously maintained when the short-circuit state is detected at time of the start of the actuation of the gas sensor 1 in the embodiment, this is not restricted but the heater current conductance amount may be increased to be a larger current conductance amount than the warming-up heater current conductance amount, for example.

Moreover, the control device 2 may set a different predetermined failure signal from a detection signal output in an ordinary actuation state to be output as the output signal of the gas sensor 1 to an outside when detecting the short-circuit state of the gas sensor 1.

While the gas sensor 1 is set to be the hydrogen sensor in the embodiment, this is not restricted but a gas sensor for detecting another gas, for example, a flammable gas such as carbon monoxide or methane may be used.

Although the bridge circuit is used for connecting the units 31 and 32 to each other in the embodiment, moreover, this is not restricted but another circuit such as a series circuit may be used and the detected value of a voltage or a current between predetermined contacts may be output, to the control device 2, as a state amount related to the resistance value R4 of the detecting unit 31.

While the heater 36 is provided between the detecting unit 31 and the temperature compensating unit 32 in the embodiment, furthermore, this is not restricted but the heater 36 may be provided between each of the units 31 and 32 and the gas introducing portion 29 in the gas detecting chamber 27, for example.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. A control device of a gas sensor for detecting a concentration of a detected gas contained in a gas to be inspected based on a difference in an electrical resistance value between a detecting unit and a compensating unit, comprising:
    a current detector for detecting a current conducted to the detecting unit and the compensating unit;
    short-circuit determination means for determining, at plural times, whether or not a detected value of the conducting current which is detected by the current detector is equal to or greater than a predetermined threshold; and
    abnormality determination means for determining an abnormal state of the detecting unit and the compensating unit, wherein
    said abnormal state is determined under such a condition that a duration time of a determination state of the detected value of the conducting current being equal to or greater than the predetermined threshold by the short-circuit detecting means is equal to or longer than a predetermined time.

2. The control device of a gas sensor according to claim 1, further comprising current conductance control means for continuously conducting the detecting unit and the compensating unit when determining that the detected value of the conducting current is equal to or greater than the predetermined threshold by the short-circuit determination means.

3. The control device of a gas sensor according to claim 1, wherein the detecting unit and the compensating unit are provided in a gas detecting chamber for introducing the gas to be inspected, the control device further comprising:
    a heater provided in the gas detecting chamber; and
    heater current conductance control means for continuing or starting to conduct the heater when it is determined that the detected value of the conducting current is equal to or greater than the predetermined threshold by the short-circuit determination means.

4. The control device of a gas sensor according to claim 1, wherein the predetermined time is equal to or longer than an upper limit time required for evaporating water present on surfaces of at least the detecting unit and the compensating unit.

* * * * *